US00PP22728P3

(12) United States Plant Patent
Mines et al.

(10) Patent No.: US PP22,728 P3
(45) Date of Patent: May 8, 2012

(54) ***DIANELLA CAERULEA×BREVIPEDUNCULATA* PLANT NAMED 'WEEPING KATE'**

(50) Latin Name: *Dianella caerulea×brevipedunculata*
Varietal Denomination: Weeping Kate

(76) Inventors: Charles Mines, Park Ridge (AU); Francis Benson, Park Ridge (AU)

( * ) Notice: Subject to any disclaimer, the term of this patent is extended or adjusted under 35 U.S.C. 154(b) by 112 days.

(21) Appl. No.: 12/658,420

(22) Filed: Feb. 11, 2010

(65) Prior Publication Data

US 2011/0197326 P1 Aug. 11, 2011

(51) Int. Cl.
*A01H 5/00* (2006.01)

(52) U.S. Cl. ..... Plt./424

(58) Field of Classification Search ..... Plt./424
See application file for complete search history.

*Primary Examiner* — Kent L Bell
(74) *Attorney, Agent, or Firm* — Paul S. Rooy PA

(57) ABSTRACT

'Weeping Kate' is a distinctive variety of *Dianella* plant which is characterized by the combination of its short to medium plant height, dense upright growth habit with flowers positioned just above the foliage, upright leaf attitude with distal weeping, year round flowering season, and violet blue flower color with violet blue berry color.

7 Drawing Sheets

Latin name of the genus and species: The Latin name of the novel variety disclosed herein is *Dianella caerulea×brevipedunculata.*

Variety denomination: The inventive variety of *Dianella caerulea×brevipedunculata* disclosed herein has been given the varietal denomination 'Weeping Kate'.

BACKGROUND OF THE INVENTION

The present invention relates to a new and distinct perennial Blue Flax Lily variety of *Dianella caerulea×brevipedunculata,* which has been given the varietal denomination of 'Weeping Kate'. Its market class is that of an ornamental grass-like plant. 'Weeping Kate' is intended for use in landscaping and as a decorative grass-like plant.

An application for plant breeders' rights for variety 'Weeping Kate' has been filed with the Australian Plant Breeders' Rights Office, under the name 'Weeping Kate' on 9 Jun. 2009 under Application No. 2009/138.

Parentage. The *Dianella caerulea×brevipedunculata* variety 'Weeping Kate' was first discovered in 2005 in an Australian nursery in Park Ridge, Queensland, Australia as part of a seed production program. 'Weeping Kate' is a result of an interspecific cross from open pollinated an unnamed plant of *Dianella caerulea* grown alongside an unnamed plant of *Dianella brevipedunculata.* The 'Indigo Bells' maternal parent, an unnamed plant of *Dianella caerulea* is characterized by a short to medium plant height (to 50 cm), flowering stem extending well above foliage and a typical seasonal spring to summer flowering period. The 'Weeping Kate' pollen parent, an unnamed plant of *Dianella brevipedunculata* is characterized by a short to medium plant height (to 50 cm), flowering stem position well below the foliage and a typical seasonal spring to summer flowering period.

In 2004, an unnamed plant of *Dianella caerulea* and an unnamed plant of *Dianella brevipedunculata.* were grown in separate adjacent open beds for the purpose of seed collection. The plants were open pollinated and each species type was collected separately for growing on to seedling stage.

Several thousand seedling plants were grown. In 2005 fifty plants were identified as having short plant heights. These plants were selected and grown to maturity for evaluation. A single plant from these was found to produce flowers from a small size. It was micropropagated and then planted out to test if the unique traits were reproduced over successive generation of vegetative reproduction. These plants were grown for 12 months and subsequently found to flower for 12 months of the year with a flowering stem presentation intermediate between that of an unnamed plant of *Dianella caerulea* and an unnamed plant of *Dianella brevipedunculata.* It was also found to have other characteristics of *Dianella brevipedunculata* including a clumping (not running) plant growth habit and resistance to root rotting that affects *Dianella caerulea,* but not *Dianella brevipedunculata.* It was subsequently named 'Weeping Kate' in Australia and given the name 'Indigo Bells' in the USA.

Asexual reproduction. 'Weeping Kate' was first asexually propagated by micropropagation in 2005, in the state of Queensland, Australia. It was asexually reproduced again from 2005 to 2009 and confirmed to be stable in character. The distinctive characteristics of the inventive variety, 'Weeping Kate', have remained stable and true to type from generation to generation through successive cycles of asexual reproduction including vegetative division and more than twenty generations in micropropagation.

SUMMARY OF THE INVENTION

'Weeping Kate' is a distinctive variety of *Dianella caerulea×brevipedunculata* which is characterized by the combination of its short to medium plant height, dense upright growth habit with flowers positioned just above the foliage, upright leaf attitude with distal weeping, year round flowering season, violet blue flower color with violet blue berry color, which is unusual for a *Dianella caerulea* or *Dianella brevipedunculata.*

BRIEF DESCRIPTION OF THE FIGURES

The photographs in the drawings were made using conventional techniques and show the colors as true as reasonably possible by conventional photography. Colors in the photographs may differ slightly from the color values cited in the detailed botanical description, which accurately describe the colors of the new *Dianella caerulea×brevipedunculata.*

DETAILED BOTANICAL DESCRIPTION OF THE PLANT

The following is a detailed botanical description of a new and distinct variety of a *Dianella caerulea×brevipedunculata* ornamental grass-like plant known as 'Weeping Kate'. The descriptions disclosed herein are based upon observations of the plant grown in 250 mm nursery pots and field plots in Queensland, Australia. The plants were approximately 12-months-old at the time of observation. All colors cited herein refer to The Royal Horticultural Society Colour Chart (The Royal Horticultural Society, London, 2007 edition).

Those skilled in the art will appreciate that certain characteristics will vary with older or, conversely, younger plants. 'Weeping Kate' has not been observed under all possible environmental conditions. Where dimensions, sizes, colors and other characteristics are given, it is to be understood that such characteristics are approximations or averages set forth as accurately as practicable. The phenotype of the variety may differ with variations in the environment such as season, temperature, light intensity, day length, cultural conditions and the like.

'Weeping Kate' is a perennial *Dianella caerulea×brevipedunculata* plant, which was produced through an innovative breeding program. After its selection, 'Weeping Kate' was asexually propagated by micropropagation. 'Weeping Kate' has dense growth, upright and compact growth habit, short rhizome form, violet blue flower color, short internodes located on short canes, flowering stems bearing flowers positioned just above the foliage which subsequently produce violet blue berries. A botanical description of 'Weeping Kate' and a comparison with other of *Dianella caerulea* and *Dianella brevipedunculata* are provided below.

Figure 1:
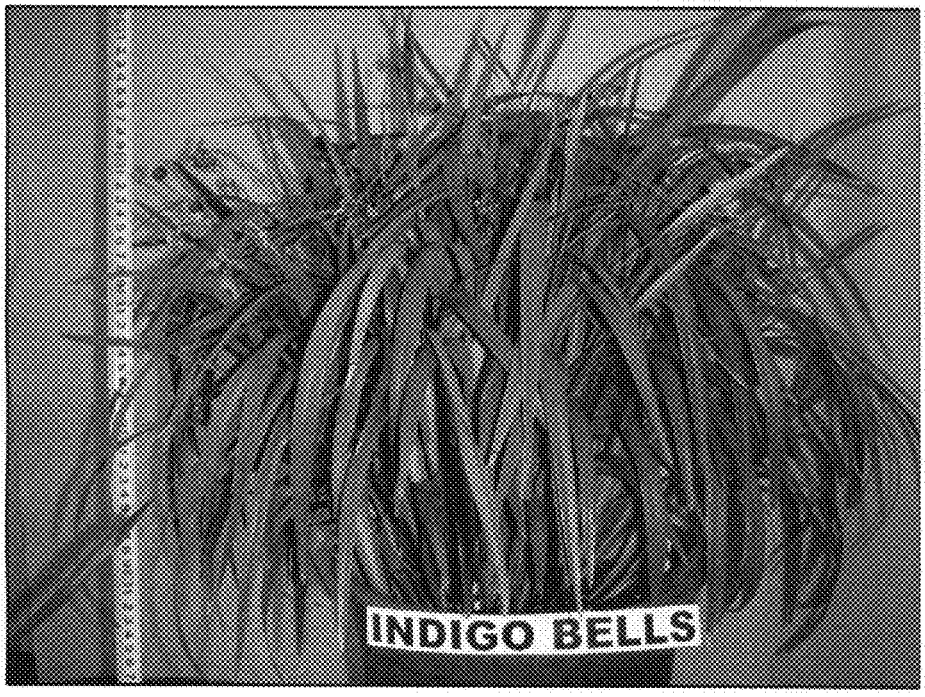
FIG. 1 shows an 'Weeping Kate' plant and illustrates the weeping leaf habit and flower position just above foliage that is characteristic of the variety.
Figure 2:
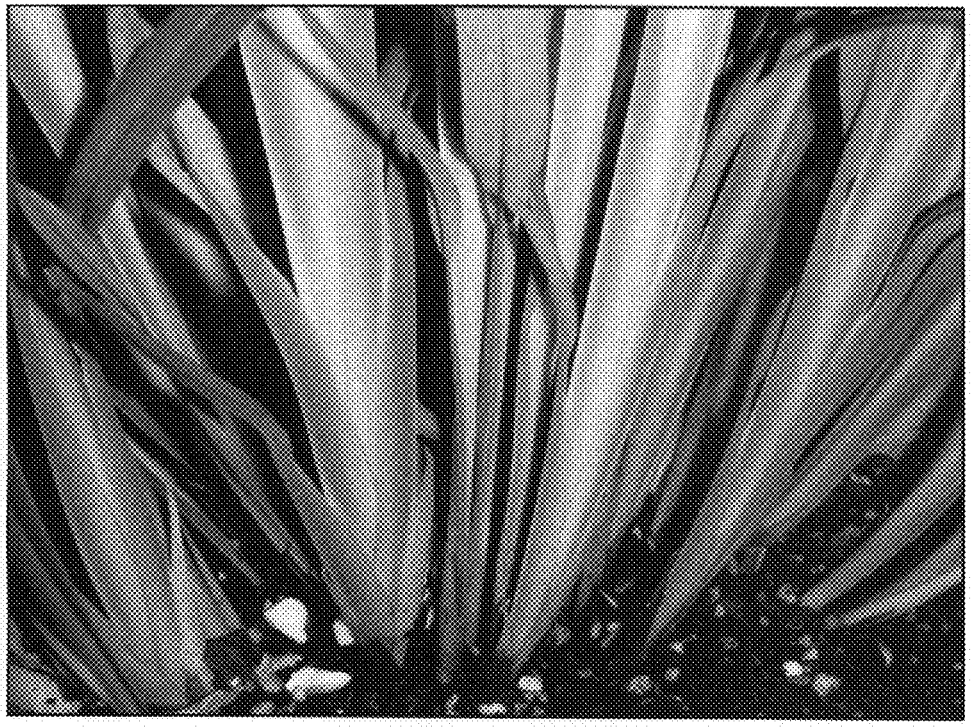
FIG. 2 shows the stem and leaf basil sheath of 'Weeping Kate'.
Figure 3:
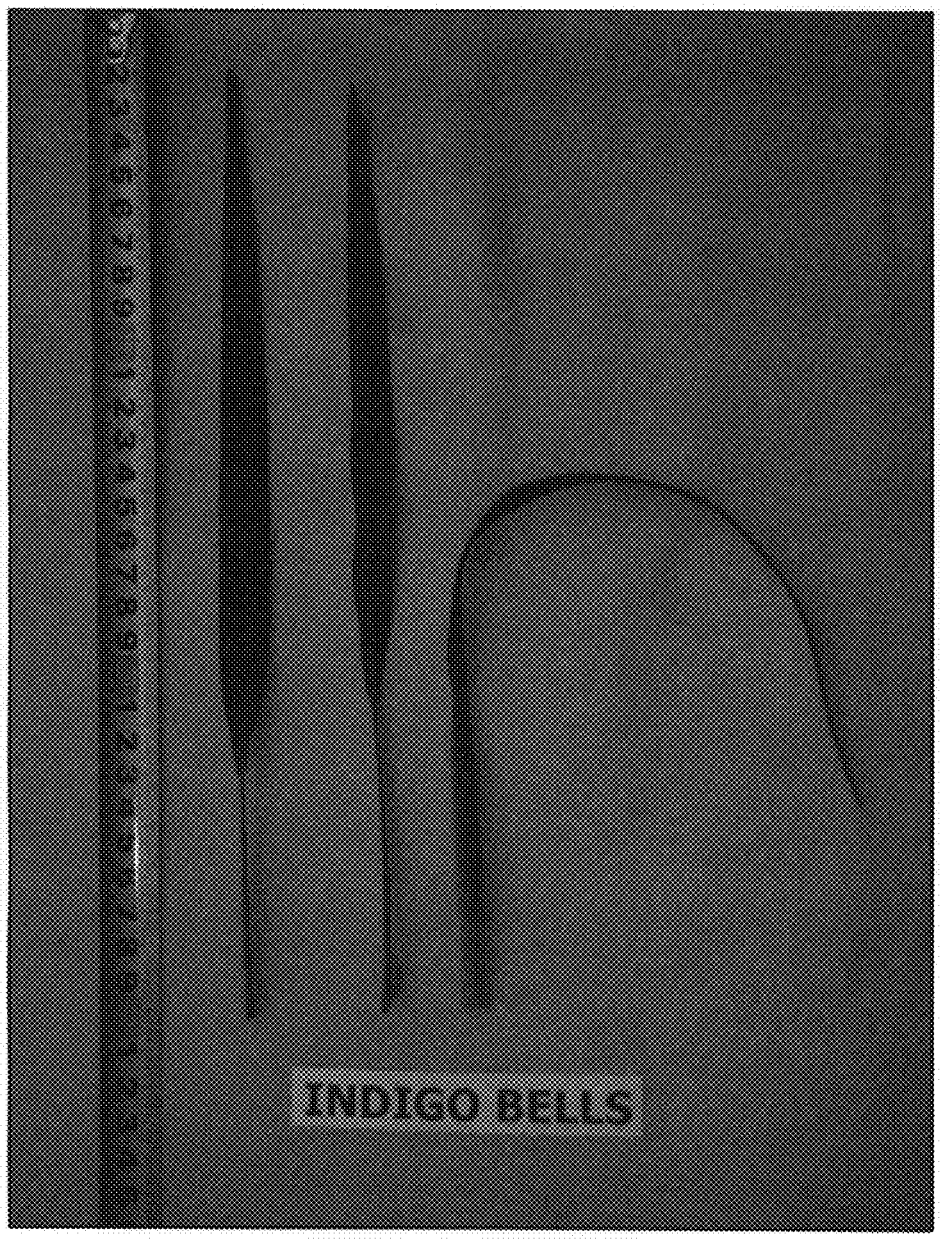
FIG. 3 shows the leaf of 'Weeping Kate'.
Figure 4:
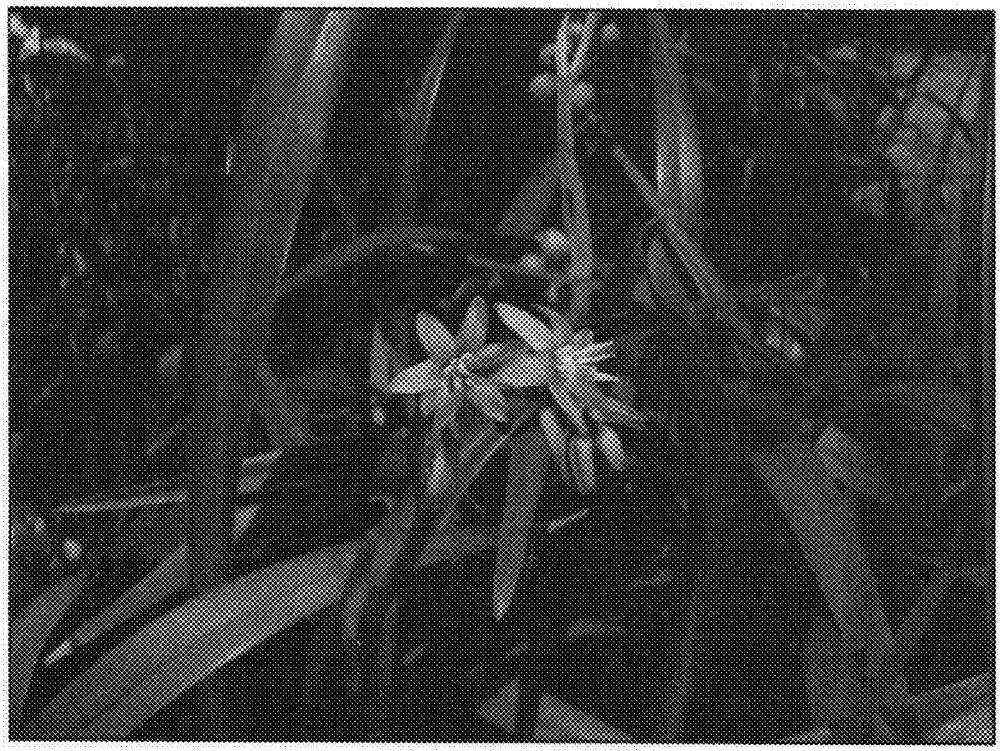
FIG. 4 shows the inflorescence of 'Weeping Kate'.
Figure 5:
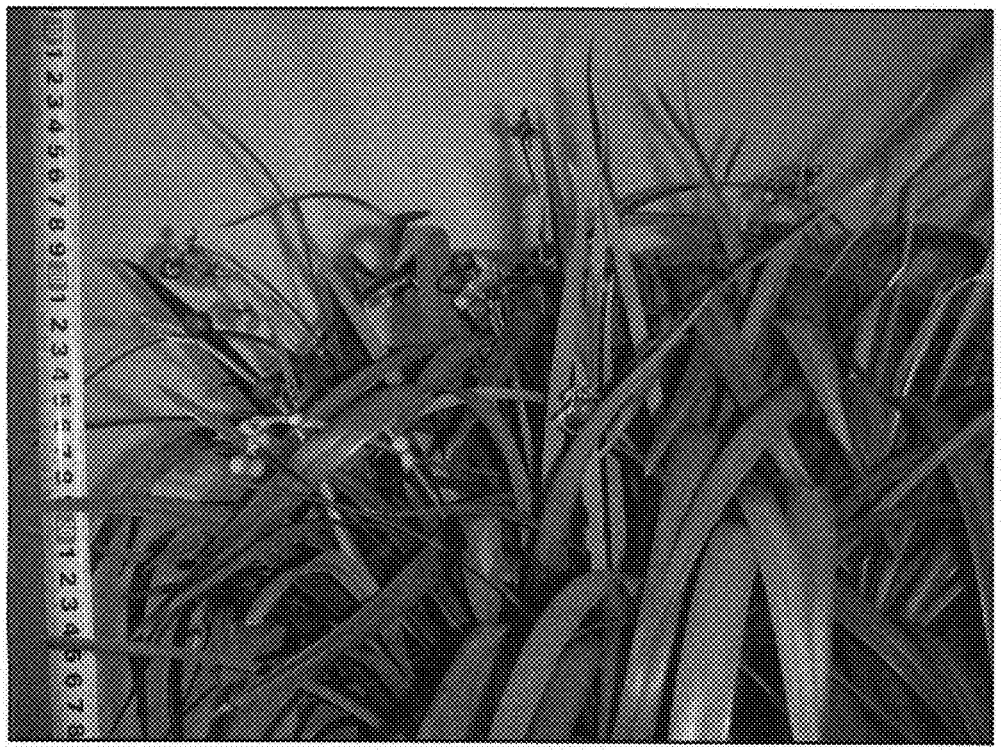
FIG. 5 shows the inflorescence position of 'Weeping Kate'.
Figure 6:
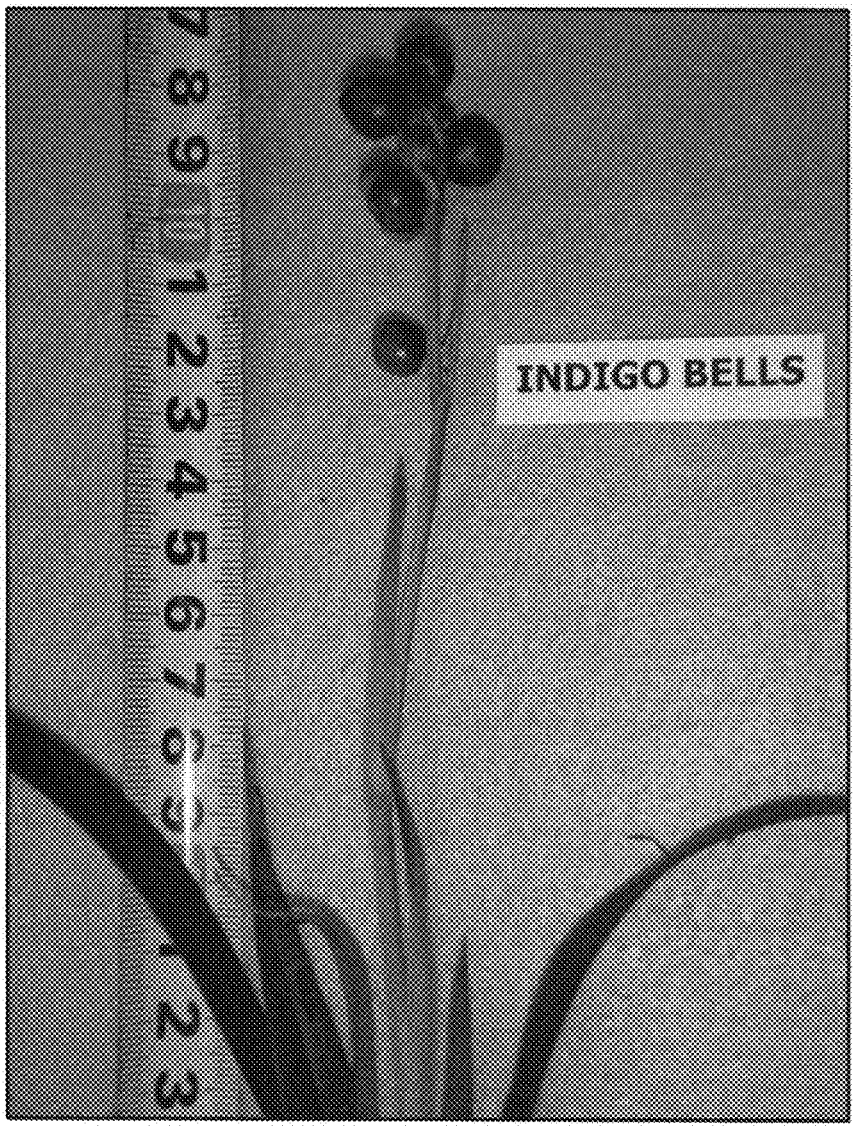
FIG. 6 shows the berry of 'Weeping Kate'.
Figure 7:
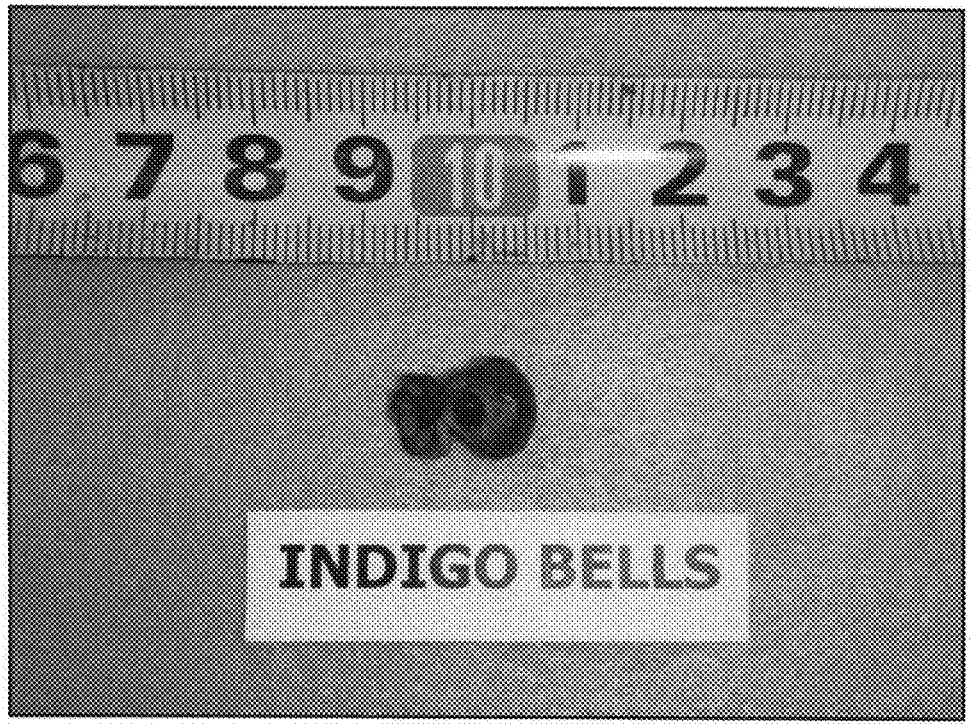
FIG. 7 shows the seed of 'Weeping Kate'.

A representative *Dianella caerulea×brevipedunculata* 'Weeping Kate' plant is shown in FIG. 1.

Technical Description of the Variety

Growth habit: 'Weeping Kate' is a rhizomatous plant forming a semi-compact tussock. Its growth habit is erect, the plant height is short to medium, (mean 50 cm), plant width is medium (55 to 60 cm) and the density of shoots is strong.

Stem: Length of internodes is short (to 10 mm). The stem length is 25 to 30 cm, its diameter 5 mm at at the base and 22 mm (including leaf sheath) halfway up. The stem color is yellow green RHS 144C to 145D.

Foliage: Leaf blade attitude erect and weeping distally, length medium (23-29 cm), width medium (13-15 mm), upper side color green (RHS N137A), lower side color yellow-green (RHS 147B to N137C), upper side glaucosity weak, upper side is slightly glossy, lower side is not glossy, shape ligulate, apex acute, cross section concave to flat, margin is entire, spines on margin absent to very weak, spines on lower side midrib absent to very weak. The leaf base is conduplicate. The leaves are sessile.

Basal sheath: Anthocyanin color absent to weak, sheath coloration yellow green (RHS 147B to RHS 144C). The basal sheath length is 12-15 cm on a mature leaf. The basal sheath width is 10-12 mm, measured from margin to midrib in conduplicate position. The basal sheath anthocyanin color approximates to grayed purple RHS 185C.

Inflorescence: The inflorescence (flower spike) is a panicle of length range 10 to 17 cm positioning the flowers and berries just above the foliage. Peduncle color is yellow green (RHS 144B). Flowering season is year round. The inflorescence — diameter is 18 to 22 mm. The number of flowers per spike is 30 to 45. The pedicel length is 4 to 6 mm, its diameter 0.5 mm, and its color is yellow green RHS 144A.

Flowers: The flower buds are 7-10 mm long and 3-4 mm wide. Bud color changes from yellow green (RHS 147B) to violet blue (RHS N89C to 93B) prior to opening. Mature flowers have 6 tepals with ovate shape. Tepal color is violet-blue (RHS N89D). Both tepal surfaces are of the same color. Anther filament color is yellow (approximately RHS 11 A). Flower diameter range is 9-13 mm. Petal attitude is horizontal to slightly reflexed. The flower shape is liliaceous. The flower depth is 7 to 10 mm.

Reproductive organs: There are six stamens. The stamen length is 5 mm. The stamen color is yellow RHS 9A. The ovary diameter is 1.5 to 2 mm at the anthesis. The ovary color is yellow green RHS 145B.

Fruit: A succulent berry, shape is globose, color of unripe berry is yellow green (RHS 144C) and color of ripe berry is approximately violet blue (RHS N89A), surface texture is smooth and glossy. Seed number is usually 6, seed color is black (RHS 203A).

Environmental tolerances: 'Weeping Kate' has shown potential for shade tolerance. The winter hardiness of 'Indigo Bells' is still undergoing testing. 'Weeping Kate' has excellent drought tolerance as for other *Dianella* varieties. After severe wilting, 'Weeping Kate' has been noted to recover with watering. 'Weeping Kate' withstands wet weather conditions and higher humidity with less root rotting disease compared to other *Dianella caerulea* varieties.

Disease resistance and susceptibility: 'Weeping Kate' has excellent tolerance to pests and diseases and good resistance to root rot, which is a common problem in *Dianella caerulea.* These features and other characteristics of the plant are apparent from the figures.

'Weeping Kate' Compared to Other Varieties of *Dianella caerulea* and *Dianella brevipedunculata*

In comparing 'Weeping Kate' with the other *Dianella caerulea* varieties including the maternal parent, 'Weeping Kate' has a more compact habit with shorter plant height than

*Dianella caerulea,* 'DCMP01' (known as 'Little Becca'), and 'DCNC0' (known as 'Becca'). 'Weeping Kate' has a shorter flower spike height (range 10-17 cm) positioned just above the foliage compared to *Dianella caerulea* (range 40-90 cm), 'DCMP01' (range 50-60 cm) and 'DCNC0' (range 80-90 cm) which has the flowers positioned well above the foliage. *Dianella caerulea,* 'DCMP01' and 'DCNC0' flower seasonally in spring to early summer whereas 'Weeping Kate' has year round flowering. 'Weeping Kate' has a violet blue flower color (RHS N89D) whereas *Dianella caerulea* (40-90 cm), 'DCMP01' has a violet blue flower color (RHS 92A to 92B) (and 'DCNC0' has a violet blue flower color (RHS 97C).

That which is claimed is:

1. A new and distinct variety of *Dianella* plant named 'Weeping Kate', substantially as described and illustrated herein.

* * * * *